United States Patent
Jun et al.

(10) Patent No.: US 12,257,186 B2
(45) Date of Patent: Mar. 25, 2025

(54) IRRIGATION AND ASPIRATION DEVICE FOR CATARACT SURGERY

(71) Applicant: The Johns Hopkins University, Baltimore, MD (US)

(72) Inventors: Albert S. Jun, Baltimore, MD (US); Joaquin Octavio De Rojas, Baltimore, MD (US); Jan McGlumphy, Baltimore, MD (US); Todd Richmond, Doylestown, PA (US)

(73) Assignee: The Johns Hopkins University, Baltimore, MD (US)

( * ) Notice: Subject to any disclaimer, the term of this patent is extended or adjusted under 35 U.S.C. 154(b) by 526 days.

(21) Appl. No.: 17/595,227

(22) PCT Filed: Apr. 23, 2020

(86) PCT No.: PCT/US2020/029571
§ 371 (c)(1),
(2) Date: Nov. 11, 2021

(87) PCT Pub. No.: WO2020/247103
PCT Pub. Date: Dec. 10, 2020

(65) Prior Publication Data
US 2022/0218889 A1    Jul. 14, 2022

Related U.S. Application Data

(60) Provisional application No. 62/858,078, filed on Jun. 6, 2019.

(51) Int. Cl.
*A61F 9/007*    (2006.01)
*A61M 1/00*    (2006.01)

(52) U.S. Cl.
CPC .......... *A61F 9/00745* (2013.01); *A61M 1/77* (2021.05); *A61M 1/84* (2021.05); *A61B 2217/005* (2013.01); *A61B 2217/007* (2013.01)

(58) Field of Classification Search
CPC ....... A61F 9/00745; A61M 1/77; A61M 1/84; A61M 2210/0612; A61B 2217/005; A61B 2217/007
See application file for complete search history.

(56) References Cited

U.S. PATENT DOCUMENTS 5,755,700 A * 5/1998 Kritzinger ............. A61F 9/0133
604/35
6,454,763 B1   9/2002 Motter et al.
(Continued)

OTHER PUBLICATIONS

International Search Report and Written Opinion—PCT/US2020/029571—ISA/RU—Jul. 23, 2020.

*Primary Examiner* — Brooke Labranche
(74) *Attorney, Agent, or Firm* — Harrity & Harrity, LLP (57) ABSTRACT

An aspiration device to be used with an irrigation-aspiration handpiece may comprise a curved body having a radius of curvature based on a human equatorial lens diameter, an interface adapted to attach the curved body to a first end of an aspiration lumen in the irrigation-aspiration handpiece, and multiple aspiration ports formed in the curved body. The multiple aspiration ports may be adapted to draw material into the aspiration lumen when a suction source is used to apply vacuum pressure at a second of the aspiration lumen while the aspiration lumen is attached to the aspiration device. The multiple aspiration ports may be arranged to distribute the vacuum pressure over an aggregate surface area of the multiple aspiration ports while the suction source applies the vacuum pressure.

20 Claims, 6 Drawing Sheets

(56) References Cited

U.S. PATENT DOCUMENTS

| | | |
|---|---|---|
| 2002/0091351 A1 | 7/2002 | Rockley |
| 2011/0015562 A1* | 1/2011 | Akahoshi ............... A61M 1/84 |
| | | 604/22 |
| 2012/0041358 A1 | 2/2012 | Mann et al. |
| 2014/0364799 A1 | 12/2014 | Beauvais et al. |
| 2016/0106580 A1* | 4/2016 | Banko ............... A61F 9/00745 |
| | | 604/22 |
| 2019/0060534 A1* | 2/2019 | Banko ............... A61M 1/7411 |

* cited by examiner

IRRIGATION AND ASPIRATION DEVICE FOR CATARACT SURGERY

RELATED APPLICATION(S)

This application is a 371 national stage of PCT Application PCT/US2020/029571 filed on Apr. 23, 2020, entitled "IRRIGATION AND ASPIRATION DEVICE FOR CATARACT SURGERY," which claims priority to U.S. Provisional Patent Application No. 62/858,078, filed on Jun. 6, 2019, the contents of which are incorporated by reference herein in its entirety.

BACKGROUND

A cataract is a clouding of the lens of the eye, which typically leads to a decrease in vision. Cataracts often develop slowly over time and can affect one or both eyes. Cataract symptoms may include faded colors, blurry or double vision, halos around light, trouble seeing at night, and/or the like. Cataracts cause half of all cases of blindness and a significant proportion of visual impairment worldwide. In many cases, cataract surgery can be performed to restore useful vision by removing and replacing the cloudy lens with an artificial intraocular lens.

SUMMARY

According to some implementations, a device may include a sleeve having a proximal end and a distal end; an aspiration lumen disposed concentrically in the sleeve and extending from the proximal end of the sleeve to the distal end of the sleeve, wherein the aspiration lumen is disposed concentrically in the sleeve to define an irrigation lumen in an annular region between the sleeve and the aspiration lumen; and a curved aspiration tip, coupled to the sleeve at the distal end of the sleeve, that has multiple aspiration ports adapted to draw material into the aspiration lumen when a suction source is used to apply vacuum pressure at a proximal end of the aspiration lumen. The curved aspiration tip may have a radius of curvature based on a human equatorial lens diameter, and the distal end of the sleeve may include one or more irrigation ports arranged to permit irrigation fluid to flow outwardly therefrom.

According to some implementations, an aspiration device may include a curved body having a radius of curvature based on a human equatorial lens diameter; an interface adapted to attach the curved body to a first end of an aspiration lumen; and multiple aspiration ports formed in the curved body. The multiple aspiration ports may be adapted to draw material into the aspiration lumen when a suction source applies vacuum pressure at a second end of the aspiration lumen while the aspiration lumen is attached to the aspiration device. The multiple aspiration ports may be arranged to distribute the vacuum pressure over the curved body while the suction source applies the vacuum pressure.

According to some implementations, a system may include a phacoemulsification machine comprising an irrigation source and a suction source; and a handpiece, coupled to the phacoemulsification machine. The handpiece may include: a body; an aspiration lumen disposed concentrically in the body of the handpiece, wherein an annular region between the aspiration lumen and the body of the handpiece defines an irrigation lumen of the handpiece; and a curved aspiration tip having multiple aspiration ports adapted to draw material into the aspiration lumen when the suction source is used to apply vacuum pressure at a proximal end of the aspiration lumen. The body may have a distal end that includes one or more irrigation ports, and the phacoemulsification machine may be adapted to cause irrigation fluid to flow from the irrigation source into the irrigation lumen and out the one or more irrigation ports.

DETAILED DESCRIPTION

The following detailed description of example implementations refers to the accompanying drawings. The same reference numbers in different drawings may identify the same or similar elements.

A cataract is a progressive cloudiness, hardening, and/or yellowing of the normally transparent lens of the eye. At birth, the natural lens is usually clear and very flexible (although not in the case of a congenital cataract, which refers to a lens opacity that is present at birth). When healthy, the lens becomes more rounded to focus on nearby objects and thinner (or stretched) to focus on objects that are farther away. Over time, however, the lens may become less flexible and begin to harden, resulting in difficulty changing a focus of the eye, which is one of the reasons why many people need reading glasses as they age (e.g., because the hardening of the lens results in difficulty focusing on nearby images such as print). Furthermore, the lens may gradually change color, eventually becoming yellowish or brownish rather than clear or transparent. Consequently, vision may acquire a yellowish or brownish tint, which creates difficulty distinguishing among certain colors and degrading the sharpness of vision as the cataract material becomes progressively cloudier. Accordingly, cataracts tend to cause progressive vision loss if left untreated, which may eventually lead to legal blindness or even total blindness.

Fortunately, even in cases where cataracts cause severe vision loss or blindness, vision can usually be restored with cataract surgery, which is among the most common surgical procedures performed worldwide. During cataract surgery, the natural lens of the eye (i.e., the cataract) is typically removed and replaced with an intraocular lens implant. One common technique used to remove the natural lens is minimally-invasive small-incision phacoemulsification (often referred to as "phaco"), in which the cataract is typically removed in two elements. The first element is the hard, central part of the cataract, referred to as the nucleus, and the second element is a softer layer that surrounds the nucleus, referred to as the cortex, which is made up of a cortical material. The goal of phaco/extracapsular cataract extraction is to remove the lens nucleus and cortex while maintaining the integrity of the lens capsule to allow placement of an intraocular lens (IOL) implant into the capsule. For example, to remove the nucleus, an ultrasonic handpiece is connected to a phaco machine, which causes a tip of the ultrasonic handpiece to vibrate at an ultrasonic frequency to emulsify the hard nucleus. In some cases, the ultrasonic handpiece or a separate instrument (sometimes called a "cracker" or "chopper") may be used to break the nucleus into smaller pieces that can be emulsified more easily. The emulsified and/or broken nucleus material is then aspirated out of the lens and eye using the same instrument, and then a different instrument referred to as an irrigation-aspiration (IA) device, an IA handpiece, and/or the like is then used to remove the cortical material by aspirating the cortical material out. The IA device is typically used to remove the cortical material because the ultrasonic handpiece has a sharp tip that is dangerous to use once the nucleus has been removed, and there is no longer a need to emulsify or break up material using ultrasonic energy after the nucleus is removed.

In general, the IA device aspirates the cortical material using vacuum pressure while simultaneously irrigating and maintaining space within the lens capsule and the anterior chamber of the eye to prevent the eye from collapsing when the cortical material is aspirated out of the eye or lens capsule. However, existing designs for IA devices pose various challenges, which include inefficiency in that existing IA devices have only a single port to remove the cortical material in small clock-hour strips shaped like pie wedges. This lengthens the time needed to remove the cortex because the single-port design limits the amount of cortical material that can be removed at a time, which means that the surgeon performing the procedure has to pass the IA device inside the capsule many times in order to remove all the cortical material. Furthermore, in some cases, removing all the cortical material may be difficult using the single-port design because there may be certain areas in the capsule that are hard to reach. This can potentially lead to post-surgical complications, as any cortical material that is left behind may cause inflammation and eventually turn white, a condition referred to as posterior capsule opacification (PCO), which may require the patient to undergo an additional laser procedure to make vision clear again. Furthermore, the single-port design carries a risk of inadvertent damage or rupture of the capsule because the surgeon has to perform additional manipulations to reach lens cortex in these hard to reach places.

Furthermore, with the single-port design, the vacuum pressure used to aspirate the cortical material is concentrated at one location, which creates a risk that the IA device will aspirate capsule material and thereby tear the capsule due to aspiration force applied to the thin and delicate capsule material while the surgeon is attempting to remove cortical material that tends to stick to the capsule. This may occur due to improper placement of the IA device and/or manipulation of the IA device in an excessive, awkward, and/or inefficient manner when attempting to remove hard-to-reach cortex (e.g., during removal of cortex, non-cortical residual lens material, and/or the like in a "subincisional" part of the capsule). For example, the concentrated vacuum pressure may pull part of the capsule into the aspiration port and potentially damage the capsule (referred to as "breaking the bag," which is among the most common complications from cataract surgery). If the capsule is damaged, any residual lens material that may still be present in the capsule can pass through the hole towards the back of the eye (to the vitreous cavity and retina). Additionally, or alternatively, vitreous gel that fills the space between the lens and the retina can come forward towards the front of the eye, which can cause traction pulling on the retina and possibly lead to retinal detachment. Accordingly, conventional coaxial single-port IA devices can be difficult to use and potentially dangerous due to an elevated risk of intra-operative and/or post-operative complications.

Some implementations described herein relate to an irrigation and aspiration (IA) handpiece tip with a curved shape that contours to the natural, round shape of a lens capsule and the lenticular and cortical material held in the capsule. For example, in some implementations, the curved tip may have a radius of curvature that is based on a human equatorial lens diameter, which provides the surgeon with more maneuverability within the lens capsule, thereby making the procedure to remove the cortical material safer and more efficient. In some implementations, the curved tip may have a flattened and laterally extended hammerhead shape (e.g., analogous to the cephalofoil head shape of a hammerhead shark) to contour to the natural shape of the lens capsule, which also makes the tip safer, more efficient, and easier to use. Furthermore, in some implementations, the hammerhead shape may provide additional surface area to accommodate multiple aspiration ports (e.g., a central aspiration port and one or more lateral aspiration ports arranged on either side of the central aspiration port). In this way, cortical material is aspirated more efficiently and a risk of damaging the capsule is reduced because vacuum pressure is distributed, pulling on cortical material at multiple places simultaneously.

In addition, as described in further detail elsewhere herein, the IA handpiece tip may be made from certain materials (e.g., silicone, metal, a non-metallic plastic or polymer, and/or the like) to reduce the risk of damaging the capsule, and various elements of the IA handpiece tip may be arranged or otherwise designed to improve safety, efficiency, and/or usability. For example, the multiple aspiration ports may have a particular diameter to maximize a rate at which cortical material is aspirated from the lens without causing a substantial reduction in suction and/or holding power by distributing vacuum pressure over a large surface area. In another example, an interface between the IA handpiece tip and a body of the IA handpiece may be flexible, bendable, or otherwise adjustable to allow for more maneuverability within the lens capsule, which allows the surgeon to reach a subincisional cortex and/or other material in hard-to-reach areas. Furthermore, due to the hammerhead shape of the IA handpiece tip being curved and/or laterally extended, the IA handpiece can be slightly rotated about a longitudinal axis to reach under the subincisional part of the lens and capsule more easily (e.g., relative to a single-port coaxial IA tip) while keeping the aspiration ports facing upward to prevent accidental aspiration of the lens capsule. In still another example, the IA handpiece tip may be removable from the body of the IA handpiece, which makes the IA handpiece tip disposable, easier to clean, and/or the like.

Figure 1A:
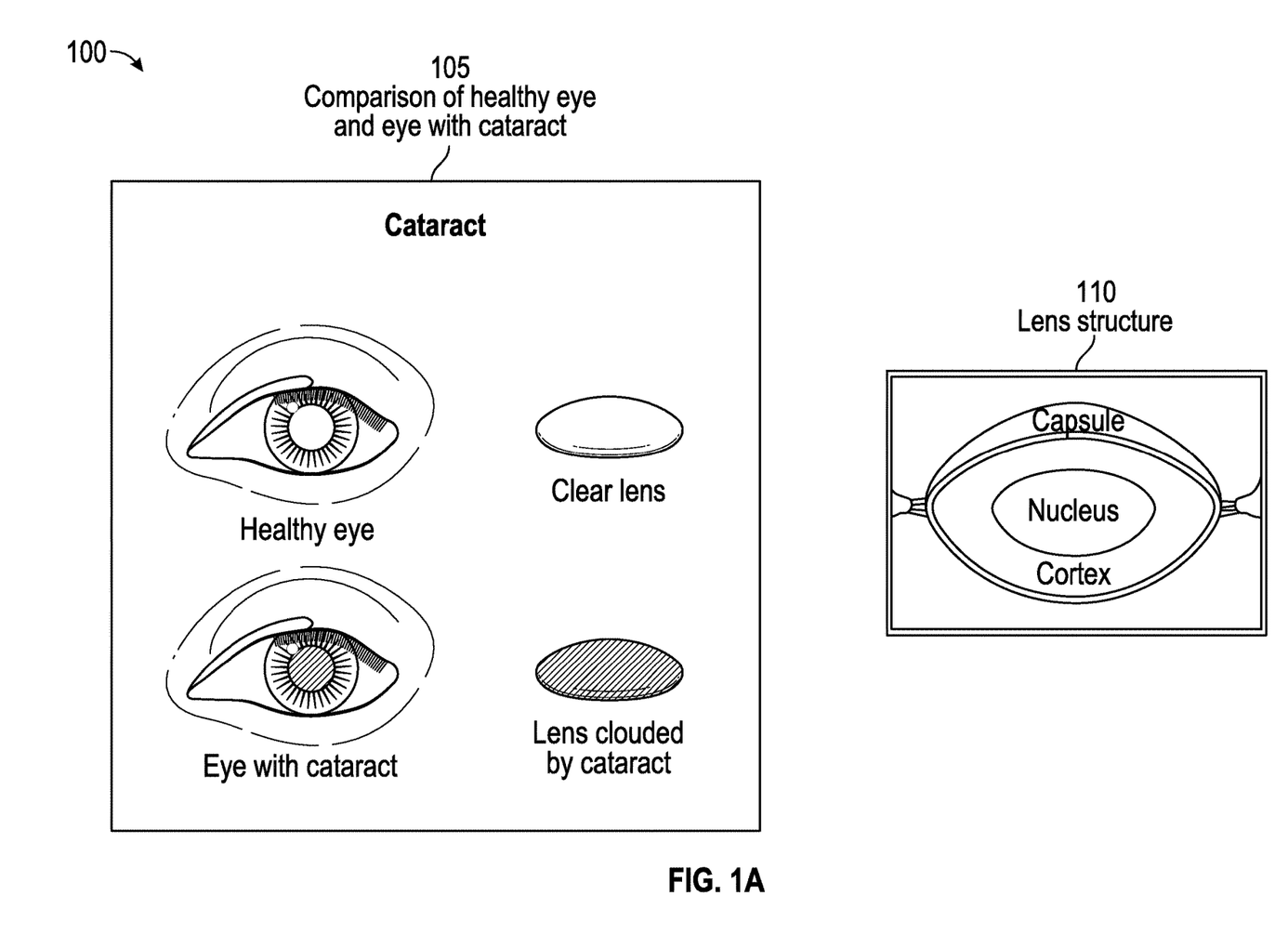
FIGS. 1A-1B are diagrams related to an example cataract surgery in which devices, systems, and/or methods described herein may be implemented.
Figure 1B:
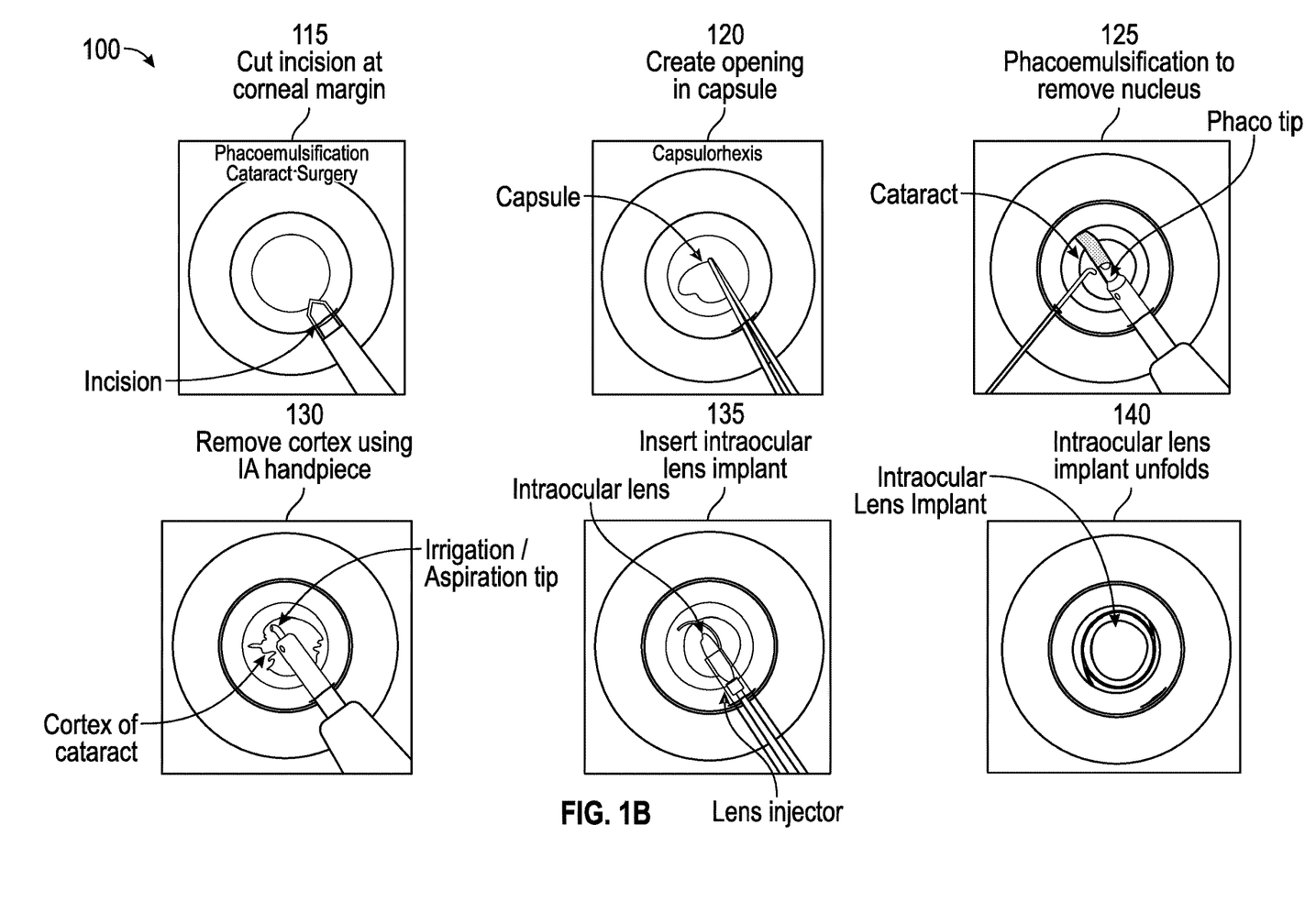

FIGS. 1A-1B are diagrams related to an example cataract surgery 100 in which devices, systems, and/or methods described herein may be implemented.

As shown in FIG. 1A, and by reference number 105, the lens in a healthy eye is clear and transparent, whereas the lens in an eye with a cataract is hardened and cloudy. Accordingly, a cataract refers to a clouding of the normally clear lens inside the eye, which can lead to significant vision impairment over time. Cataracts tend to be very common in older people, as the lens hardens and becomes cloudy as lens proteins denature and degrade over time, although certain types of cataracts can also occur in younger people (e.g., congenital cataracts, post-traumatic cataracts, cataracts caused by radiation exposure, drug-induced cataracts, and/or the like). In general, the eye enables a person to see by allowing light to pass through the cornea at the front of the eye, and the lens focuses the light onto the retina, which is a delicate tissue that lines the inside of the back of the eye. The retina converts the light into electrical signals that travel along the optic nerve to the brain, which interprets the electrical signals as images so that a person can see.

As shown in FIG. 1A, the lens in a healthy eye is clear and transparent and permits light to easily pass through, producing a sharply focused image on the retina. However, when a cataract forms, the cloudy lens causes light to be scattered and/or blocked, causing foggy images, blurry images, discolored images, increased sensitivity to bright light, glare, and/or other vision impairments up to and including blindness. In the early stages of a cataract, there may be no symptoms or vision impairment, but as the cataract progresses, the symptoms become noticeable and progressively worsen. When a cataract patient starts to experience significant vision impairment, reduced quality of life, and/or the like, an evaluation may be performed to determine whether the cataract patient is a suitable candidate for cataract surgery (e.g., based on a degree of vision impairment due to the cataract, other factors related to eye health such as whether the patient has pre-existing glaucoma or retinal detachment, whether the patient is taking medications that may result in the patient developing surgical complications, and/or the like). When the patient is determined to be a suitable candidate for cataract surgery, the lens that is clouded by the cataract may be surgically removed and replaced with an intraocular lens implant.

As shown in FIG. 1A, and by reference number 110, the lens may be structured as a biconvex disk located behind the iris and in front of the vitreous body. The lens is circumferentially suspended inside the eye to the ciliary body by cords called zonules. The ciliary body is a circular structure that lines the inside of the eye, which contains a muscle that tenses or relaxes the zonules to change the shape and thickness of the lens. This controlled transformation of the lens shape alters the angle of the light entering and exiting the lens, which allows a healthy eye to focus images nearby or in the distance onto the retina through an action referred to as accommodation.

As shown by reference number 110, the lens has three major parts, referred to as a nucleus, a cortex, and a capsule, which are circumferentially layered. In particular, the nucleus is at the center of the lens and contains proteins that are present from birth. As mentioned above, the nucleus generally hardens over time, which can eventually lead to or contribute to cataract formation. As a person ages, layers of transparent fibers are created and layered around the nucleus to create the cortex (or cortical material), which is much softer than the nucleus. The capsule is a transparent elastic membrane that surrounds the nucleus and the cortex. During phacoemulsification cataract surgery, a procedure described in more detail elsewhere herein, an anterior part of the capsule is opened to enable access to and removal of the nucleus and the cortex, while the capsule is maintained to serve as a "bag" to hold an intraocular lens implant.

As shown in FIG. 1B, and by reference number 115, a phacoemulsification cataract surgery may include cutting a small incision at a corneal margin. For example, the incision is usually about 3 millimeters in length, and is generally self-sealing whereby the wound naturally heals after surgery with no stitches. This wound may be started in the clear portion of the cornea, or the wound can be started from a more posterior position (e.g., from the limbus, the sclera, and/or the like). As further shown in FIG. 1B, and by reference number 120, the phacoemulsification cataract surgery may further include a capsulorhexis, which refers to a technique in which a central hole or opening is created in the capsule to provide access to the nucleus and the cortex to be removed from the lens. The capsulorhexis technique is performed to create access for removing lenticular material while maintaining integrity of the capsule that will hold the intraocular lens to be implanted to replace the clouded lens being removed.

As further shown in FIG. 1B, and by reference number 125, the phacoemulsification cataract surgery may include a phacoemulsification step to remove the hard nucleus at the center of the lens using a phaco handpiece. For example, the phaco handpiece may be connected to a phaco machine that uses ultrasound energy to break down and/or emulsify the nucleus, and a vacuum is attached to the phaco handpiece in order to aspirate broken down and/or emulsified pieces of the nucleus. As further shown in FIG. 1B, and by reference number 130, cortical aspiration may then be performed to remove the cortex using an irrigation-aspiration (IA) handpiece, which may also be attached to the phaco machine.

During the cortical aspiration, the IA handpiece is used to pull at the cortex and draw the cortical material into an aspiration lumen while an irrigation fluid (e.g., a balanced salt solution) is injected into the capsule. In particular, as mentioned elsewhere herein, the irrigation fluid is injected to maintain the anterior and/or posterior chamber(s) and prevent the eye from collapsing as the cortical material is aspirated. The cortical aspiration tends to be the step in the cataract surgery where the capsule is most likely to be torn or damaged, as the cortical material sticks to the capsule and may be difficult to reach. As mentioned above, a tear in the capsule may result in vitreous entering the anterior chamber, which could lead to retinal detachment, and/or lenticular material passing towards the back of the eye. Accordingly, in some implementations, an IA handpiece and/or one or more components of an IA handpiece used during the cortical aspiration may be designed to increase the efficiency and/or safety of the cortical aspiration, as described in more detail elsewhere herein. After all of the cortical material has been removed, the capsule may be empty and ready for implantation of the intraocular (replacement) lens.

As further shown in FIG. 1B, and by reference number 135, the intraocular lens implant may be inserted into the empty capsule. The intraocular lens implant may include an optic part and two arms or haptics branching from the side of the optic part to hold the entire structure of the intraocular lens implant in place within the capsular bag. For example, to fit the optic part and the haptics into the small incision, the intraocular lens implant is typically folded and injected into the eye through a cylindrical tube (e.g., a lens injector). As further shown in FIG. 1B, and by reference number 140, once inserted, the haptics of the intraocular lens implant unfold. At that point, the IA handpiece is inserted to remove any additional viscoelastic material that has been inserted into the eye to keep the eye full during the procedure. In particular, the IA handpiece is used to remove this additional material because leaving the additional material in the eye would create high pressure in the eye, potentially leading to complications. The surgeon then hydrates the corneal incision to cause the tissues of the cornea to expand and press against one another, sealing the wound and making the wound water-tight without sutures.

As indicated above, FIGS. 1A-1B are provided merely as one or more examples. Other examples may differ from what is described with regard to FIGS. 1A-1B.

Figure 2A:
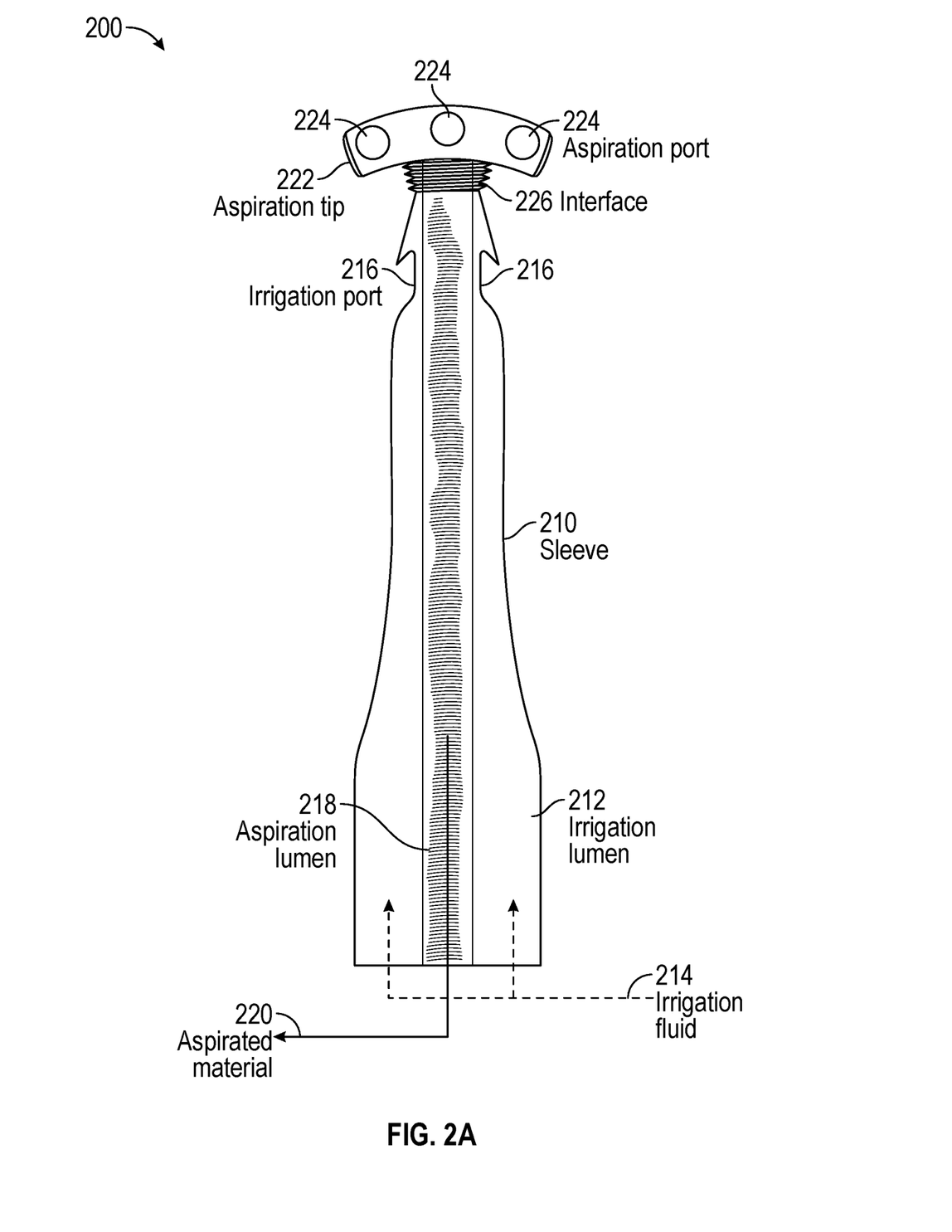
FIGS. 2A-2B are diagrams of one or more example implementations of an irrigation and aspiration handpiece described herein.
Figure 2B:
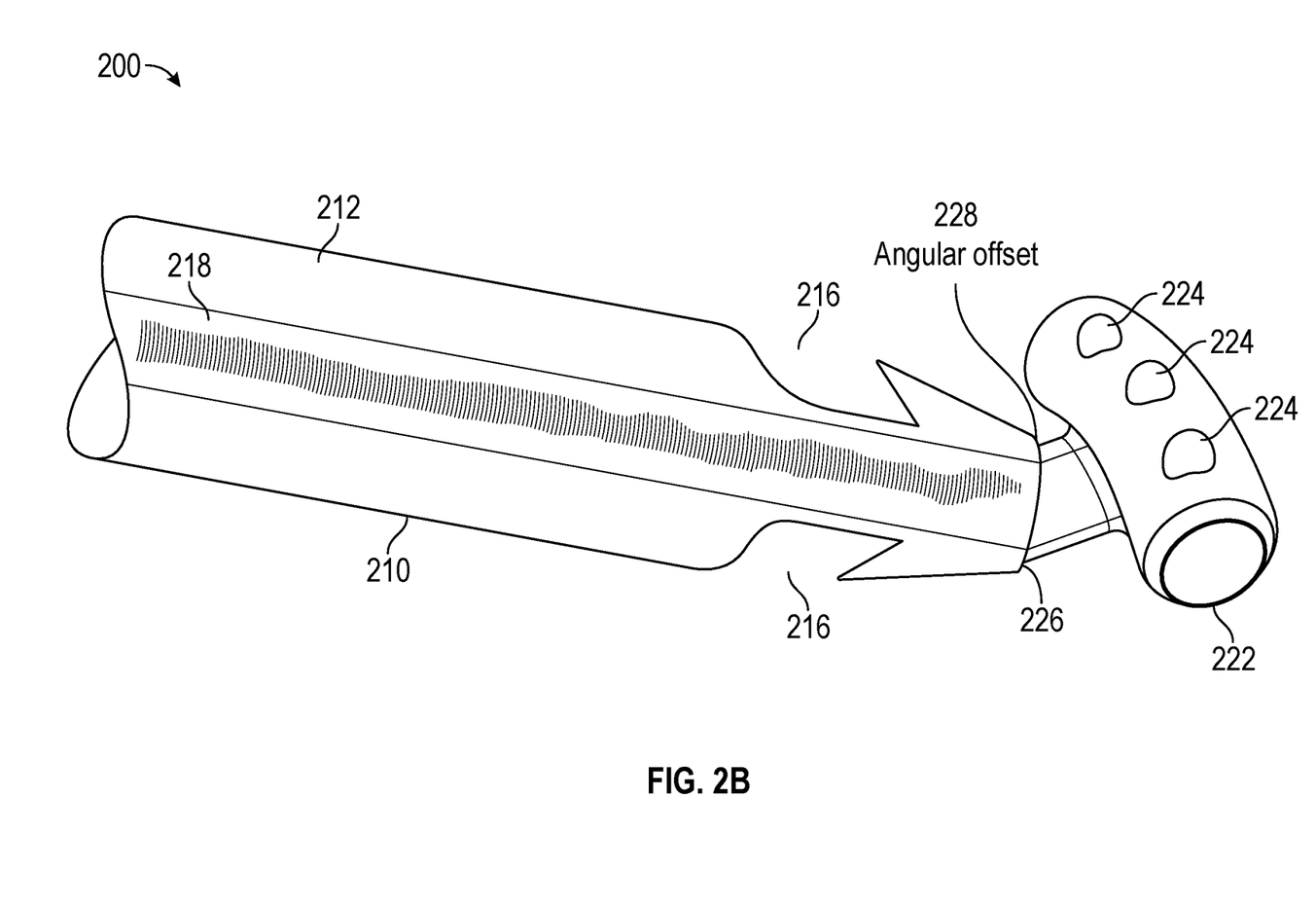

FIGS. 2A-2B are diagrams of one or more example implementations of an irrigation and aspiration (IA) handpiece 200 described herein. In general, the IA handpiece 200 may be used to remove cortical material from a lens of a cataract surgery patient after a nucleus has been removed from the lens of the cataract surgery patient via phacoemulsification. Additionally, or alternatively, the IA handpiece 200 may be used to remove retained viscoelastic material from the anterior chamber of the eye after an intraocular lens implant has been inserted into the eye of the cataract surgery patient. For example, the viscoelastic material is a synthetic material often added prior to the capsulorhexis step of cataract surgery to make space for the instruments used during the cataract surgery beneath the delicate endothelium of the cornea and above the fragile capsule. Accordingly, after the cataract lens has been removed, the viscoelastic material can be added prior to insertion of the intraocular lens. Subsequently, the IA handpiece 200 may be used to aspirate out this (synthetic) viscoelastic material, as leaving the viscoelastic material in the eye can lead to increased intraocular pressure after the cataract surgery.

As shown in FIG. 2A, the IA handpiece 200 may include a sleeve 210 having a proximal end and a distal end. In some implementations, the sleeve 210 may be made from silicone, plastic, and/or another suitable material. As further shown in FIG. 2A, the IA handpiece 200 includes an irrigation lumen 212, and irrigation fluid 214 may enter the irrigation lumen 212 through an opening at the proximal end of the sleeve 210 and exit the irrigation lumen 212 through a set of irrigation ports 216. Furthermore, the irrigation lumen 212 may be formed around an (inner) aspiration lumen 218, which may be a metal rod, a plastic tube, a canal, a duct, and/or other suitable structure to provide a channel through which aspirated material 220 may pass. For example, in some implementations, the irrigation lumen 212 and the aspiration lumen 218 may have respective openings arranged to receive tubing and/or other suitable equipment. Accordingly, the irrigation fluid 214 may flow from a fluid source (e.g., an intravenous fluid bag, a pressure bag, and/or the like) and into the irrigation lumen 212 through the tubing, and the aspirated material 220 may be drawn into the aspiration lumen 218 through an aspiration tip 222 having multiple aspiration ports 224 before passing through the tubing and into a waste bag. In some implementations, the aspiration tip 222 may be made from silicone, metal, a non-metallic plastic or polymer, and/or the like.

As further shown in FIG. 2A, the aspiration lumen 218 may extend from the proximal end of the sleeve 210 to the distal end of the sleeve 210, and the aspiration lumen 218 may be disposed concentrically in the sleeve 210 to define the irrigation lumen 212 in an annular region between the sleeve 210 and the aspiration lumen 218. As further shown in FIG. 2A, the aspiration tip 222 may have a curved shape, with a body portion that is flattened and laterally extended to form a hammerhead shape (e.g., a shape similar to the head of a hammerhead shark, often referred to as a cephalofoil) to contour to the natural shape of a lens capsule, which makes the aspiration tip 222 safe, efficient, and easy to use to remove material (e.g., cortical material, viscoelastic material, and/or the like) from the eye of a cataract surgery patient.

As further shown in FIG. 2A, an interface 226 may couple the aspiration tip 222 to the sleeve 210 at the distal end of the sleeve 210, and the multiple aspiration ports 224 may be adapted to draw material to be aspirated into the aspiration lumen 218 when a suction source (e.g., a pump provided in a phaco machine attached to the IA handpiece 200) is used to apply vacuum pressure at a proximal end of the aspiration lumen 218. As shown, the set of irrigation ports 216 may be arranged at the distal end of the sleeve 210 to permit the irrigation fluid 214 to flow outwardly therefrom (e.g., the irrigation fluid 214 flows into the capsule of the lens to maintain a balance between fluid entering and exiting the eye).

In some implementations, the aspiration tip 222 may have a radius of curvature based on a human equatorial lens diameter, and the radius of curvature in combination with the flattened and laterally extended hammerhead design may provide the aspiration tip 222 with a curved shape that matches or otherwise contours with the natural shape of the lens capsule. For example, the equatorial lens diameter is usually about 6.5 millimeters at birth, which typically reaches about 9.0 to 10.0 millimeters at adulthood. In some implementations, the radius of curvature may have a value that provides a curvature that is relatively close but sharper than the human equatorial lens diameter for the intended cataract surgery patient (e.g., by an amount that satisfies a threshold). In this way, the curved aspiration tip 222 may contour to the natural curvature of the capsule for the intended cataract surgery patient as well as patients that may have a slightly smaller capsule or a slightly larger capsule. For example, assuming that the intended cataract surgery patient is an adult with an equatorial lens diameter of about 9.0 millimeters (corresponding to a radius of about 4.5 millimeters), an outer arc of the curved aspiration tip 222 may have a radius of curvature less than or equal to the radius of curvature of the average cataract/natural lens (i.e., ≤about 4.5 millimeters). For example, a radius of curvature of about 3.5 millimeters may contour with the natural shape of capsules in the typical range from about 9.0 to 10.0 millimeters, providing the surgeon with maximum maneuverability as well as the ability to work in smaller-than-average eyes. Additionally, or alternatively, the radius of curvature may have an intermediate value between the radius of curvature of the lens equator and the capsulorhexis to account for the usage of the IA handpiece 200 in a region between the lens equator and an edge of the capsulorhexis.

In some implementations, the aspiration tip 222 may be integrally coupled to the sleeve 210, in which case the interface 226 between the aspiration tip 222 and the sleeve 210 may be substantially continuous (e.g., the aspiration tip 222, the interface 226, the aspiration lumen 218, and/or the sleeve 210 may be constructed as a single piece). Additionally, or alternatively, the interface 226 between the aspiration tip 222 and the sleeve 210 may permit the aspiration tip 222 to be removed or otherwise decoupled from the sleeve 210. For example, the interface 226 may permit the aspiration tip 222 to be screwed onto and/or off of the sleeve 210, snapped onto and/or off of the sleeve 210, and/or the like. In this way, the aspiration tip 222, the aspiration lumen 218, and/or other components of the IA handpiece 200 may be easily cleaned, sterilized, and/or the like. Additionally, or alternatively, the removable feature may allow for the aspiration tip 222 to be constructed from a disposable material, which may make the IA handpiece 200 less expensive and more accessible (e.g., to treat cataract patients in developing countries).

In some implementations, the aspiration tip 222 may be constructed in different sizes to accommodate variations in the size and/or shape of eyes of different cataract surgery patients. For example, although cataracts generally tend to develop as a person ages, cataracts can be present at birth (e.g., in the case of congenital cataracts) or form at younger ages due to other circumstances such as blunt trauma, radiation exposure, and/or the like. Accordingly, in some implementations, the aspiration tip 222 may be constructed in different sizes (e.g., small, medium, large, and/or the like) with varying radii of curvature to accommodate cataract surgery patients with different equatorial lens diameters (e.g., young children, adolescents, adults, and/or the like). Accordingly, in some implementations, the interface 226 permitting the aspiration tip 222 to be removed from the sleeve 210 may allow the aspiration tip 222 to be swapped out for another aspiration tip 222 of a different size depending on the intended patient. Additionally, or alternatively, where the aspiration tip 222 is integrally coupled to (e.g., not removable from) the sleeve 210, different IA devices 200 may be constructed with aspiration tips 222 of various sizes.

As further shown in FIG. 2A, the flattened and laterally extended hammerhead shape of the aspiration tip 222 may provide the aspiration tip 222 with a surface area that can accommodate the multiple aspiration ports 224, which may enable material (e.g., cortical material, viscoelastic material, and/or the like) to be drawn into the aspiration lumen 218 and removed as aspirated material 220 faster, more efficiently, and/or the like relative to a single-port design. For example, as the suction source is used to apply vacuum pressure at the proximal end of the aspiration lumen 218, the vacuum pressure may be distributed among the multiple ports 224, which may simultaneously draw cortical material, viscoelastic material, lenticular material, and/or the like from the capsule into the aspiration lumen 218. The vacuum pressure may allow the surgeon or another user operating the IA handpiece 200 to remove the material from the capsule, and the aspiration ports 224 may have a diameter that provides an aggregate surface area to maximize a rate at which material is drawn into the aspiration lumen 218 while also ensuring that there is sufficient holding force to efficiently draw the material into the aspiration lumen 218.

For example, the multiple aspiration ports 224 may be spread out across the aspiration tip 222 to remove large sections of material (e.g., a whole quadrant or half the cortical material in the capsule) in a single pass, rather than small wedges, which allows all of the cortex to be removed in fewer passes relative to a single-port design (e.g., in two or three passes). In contrast, when removing the cortex using a conventional (single-port) IA handpiece, the IA handpiece is typically placed under an edge of the capsulorhexis and used to pull at the cortex from within the capsule, closer to the lens equator, while moving in a circumferential manner. For example, when using a single-port IA handpiece, the surgeon may attempt to grab two or three clock hours of cortex at a time by moving circumferentially before bringing the IA handpiece radially toward the center of the eye, which would require the surgeon to perform several passes (e.g., five or more) in order to remove all the cortical material. In this way, by providing a design with the multiple aspiration ports 224, the aspirated material 220 may be removed more efficiently (e.g., in fewer passes and in larger sections), which allows for faster and safer cortical cleanup and a reduced likelihood that there will be residual cortical material in the capsule. Consequently, the multiple ports 224 may reduce surgical time, which may reduce a likelihood of inflammation in the eye after the cataract surgery, which in turn may reduce a probability that the cataract surgery patient will develop ocular hypertension, uveitis, corneal edema, macular edema, and/or posterior capsule opacification (PCO) that may require the patient to undergo additional treatments or interventions (e.g., a follow-up laser procedure) to make vision clear again.

In some implementations, as mentioned elsewhere herein, the aspiration ports 224 may have a diameter that provides an aggregate surface area to maximize a rate at which material is drawn into the aspiration lumen 218 while also ensuring that there is sufficient holding force to efficiently draw the material into the aspiration lumen 218. For example, in some implementations, the diameter of the aspiration ports 224 may be in a range from about 0.20 millimeters to about 0.30 millimeters, where diameters towards the lower end of the above-mentioned range may provide higher suction and/or holding force and diameters towards the higher end of the above-mentioned range may provide more surface area to allow more aspirated material 220 to pass through. However, the diameters towards the higher end of the above-mentioned range may also exhibit relatively lower suction and/or holding force, meaning that the aspirated material 220 may be drawn into the aspiration lumen 218 at a slower rate than diameters towards the lower end of the above-mentioned range. Accordingly, although the diameter of the aspiration ports 224 may generally fall within the range from about 0.20 millimeters to about 0.30 millimeters, a diameter of approximately 0.25 millimeters may provide an optimal tradeoff between maximizing the surface area available to draw aspirated material 220 into the aspiration lumen 218 and maintaining a sufficiently high suction and/or holding force to ensure that the aspirated material 220 is drawn in at an efficient rate. Furthermore, a diameter closer to the mid-point of the range may avoid a need to operate the suction source (e.g., a phaco machine) at a high vacuum level, which may reduce a risk of damaging the capsule when removing the cortex, reduce energy consumed by the suction source, and/or the like.

In some implementations, the multiple aspiration ports 224 may be arranged on the aspiration tip 222 in a manner that may distribute vacuum pressure applied at the suction source over the body of the aspiration tip 222, which may further reduce a risk of damaging the capsule when operating the IA handpiece 200. For example, as shown in FIG. 2A, the multiple aspiration ports 224 include a central port and one or more lateral ports arranged on either side of the central port, whereby the vacuum pressure is distributed across the central port and the lateral ports on either side of the central port, which makes the IA handpiece 200 safer in addition to being more efficient than single-port designs. For example, as shown in FIG. 2A, the IA handpiece 200 includes three aspiration ports 224, with one aspiration port 224 arranged on either side of the central aspiration port 224. Alternatively, in another design, the IA handpiece 200 may include five aspiration ports 224, with two lateral aspiration ports 224 arranged on either side of the central aspiration port 224. In such a design, the diameter of the aspiration ports 224 may be reduced relative to the above-mentioned range to ensure that there is sufficient suction and/or holding power to draw in aspirated material 220, with the additional two aspiration ports 224 providing more aggregate surface area to compensate for the smaller diameter. In other designs, the IA handpiece 200 may have additional aspiration ports 224, fewer aspiration ports 224, and/or differently arranged aspiration ports 224 than shown in FIGS. 2A-2B (e.g., the IA handpiece 200 may have an even number of aspiration ports 224, such as two, four, six, or more aspiration ports 224).

Furthermore, the aspiration ports 224 may be arranged such that an inter-port spacing results in an efficient distribution of vacuum pressure among the aspiration ports 224. For example, in a three-port design (e.g., as shown in FIGS. 2A-2B) with the aspiration ports 224 having diameters in a range from about 0.20 millimeters to about 0.30 millimeters, a spacing between the central aspiration port 224 and each lateral aspiration port 224 may be in a range from about 0.25 millimeters to about 0.30 millimeters, with a spacing between the lateral ports 224 and a side of the aspiration tip 222 in a range from about 0.20 millimeters to about 0.30 millimeters. Accordingly, based on these example dimensions, the aspiration tip 222 may have a total width in a range from about 2.0 millimeters to about 3.0 millimeters.

As shown in FIG. 2B, and by reference number 228, the interface 226 may provide an angular offset between the aspiration tip 222 and the sleeve 210 such that the aspiration tip 222 is displaced from a longitudinal axis of the sleeve 210 (e.g., according to an angular offset in a range from about 10 degrees to about 90 degrees, or from about 30 degrees to about 45 degrees). For example, in some implementations, the interface 226 may be flexible, bendable, or otherwise adjustable to permit the aspiration tip 222 to be displaced from the longitudinal axis of the sleeve 210 such that the angular offset can be adjusted in a range from about 10 degrees to about 90 degrees, from about 30 degrees to about 45 degrees, and/or the like. Additionally, or alternatively, in some implementations, the interface 226 may provide a fixed angular offset between the aspiration tip 222 and the sleeve 210 (e.g., in implementations in which the aspiration tip 222, the interface 226, the sleeve 210, and/or the like are constructed as a single piece). In either case, the angular offset between the aspiration tip 222 and the longitudinal axis of the sleeve 210 may allow the aspiration tip 222 to be inserted at a subincisional cortex (i.e., under an incision in the capsule), which allows the subincisional cortex to be removed more easily. For example, the angular offset may allow the IA handpiece 200 to be turned towards the subincisional cortex so that the aspiration ports 224 are able to reach under the incision in order to safely remove the subincisional cortical material while also maintaining the aspiration ports 224 in an orientation facing towards the surgeon and away from the posterior capsule.

As indicated above, FIGS. 2A-2B are provided merely as one or more examples. Other examples may differ from what is described with regard to FIGS. 2A-2B.

Figure 3:
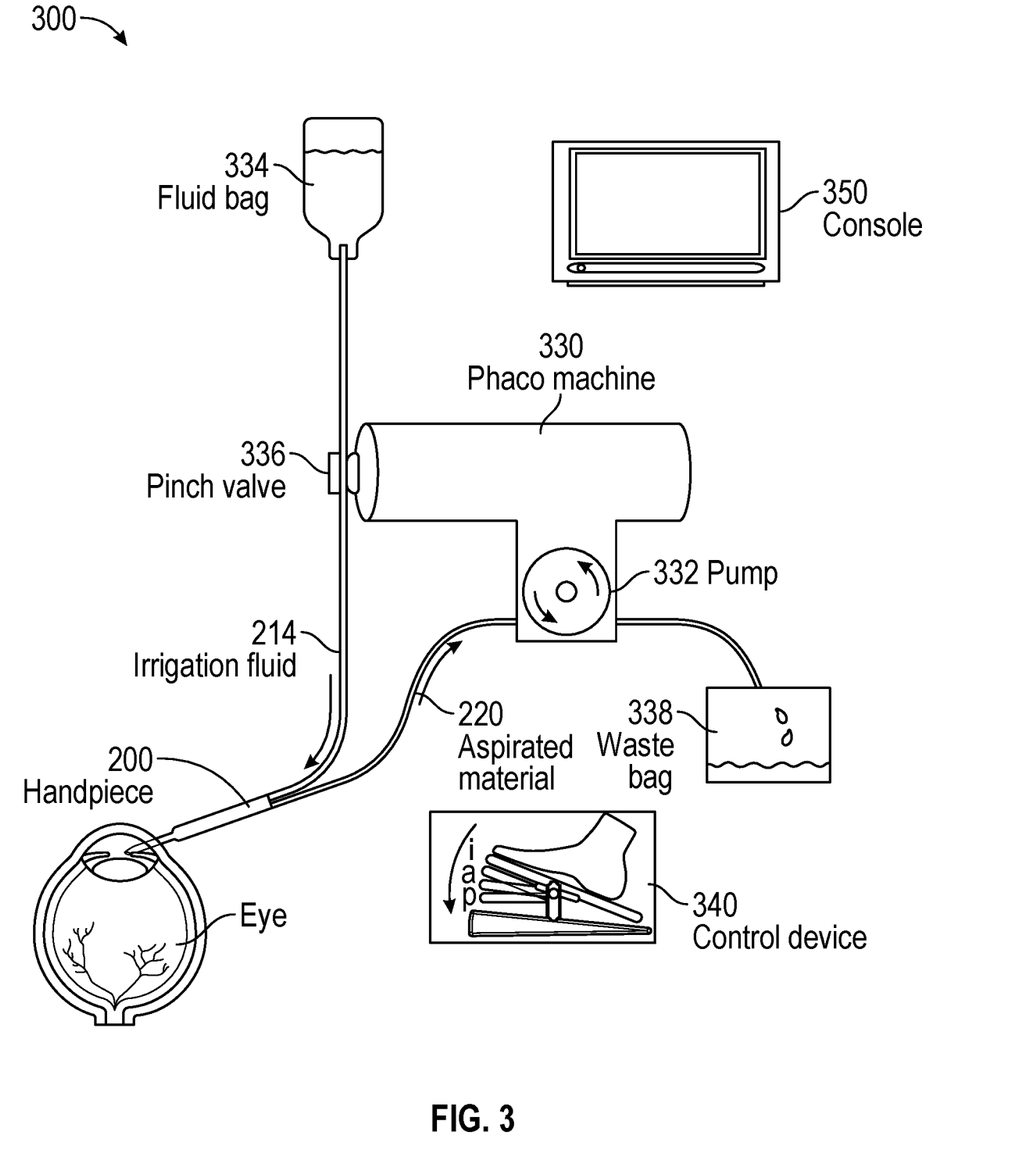
FIG. 3 is a diagram of an example environment in which devices, systems, and/or methods described herein may be implemented.

FIG. 3 is a diagram of an example environment 300 in which devices, systems, and/or methods described herein may be implemented. As shown in FIG. 3, environment 300 may include a phacoemulsification (phaco) machine 330 that can be connected to a handpiece 200 and operate in various modes to remove a natural lens from an eye of a cataract surgery patient, a control device 340 (e.g., a foot pedal) that can control a mode in which the phaco machine 330 operates, and a console 350 that can be used to control various settings or parameters associated with the phaco machine 330. Devices of environment 300 may interconnect via wired connections, wireless connections, or a combination of wired and wireless connections.

For example, the phaco machine 330 may operate in an irrigation mode when the control device 340 is set to a first position, which may cause a pinch valve 336 to open and thereby allow irrigation fluid 214 (e.g., a balanced salt solution) to flow from a fluid bag 334 into an irrigation lumen of the handpiece 200. Furthermore, the phaco machine 330 may operate in an irrigation-aspiration mode when the control device 340 is set to a second position, which may activate a pump 332 (e.g., a peristaltic or Venturi pump) to apply suction to an aspiration lumen of the handpiece 200 and thereby cause aspirated material 220 to be removed from the eye and deposited in a waste bag 338. In some implementations, the phaco machine 330 may be operated in the irrigation mode and/or the aspiration mode when the handpiece 200 is used to remove cortical material from the eye after a nucleus has been removed via phacoemulsification and/or to remove viscoelastic material from the eye after the cortical material has been removed and an intraocular lens implant has been inserted into the lens capsule of the cataract surgery patient.

Furthermore, in some implementations, the phaco machine 330 may operate in a phacoemulsification mode when removing the nucleus from the eye. In such cases, a different handpiece with a vibrating tip (e.g., a phaco handpiece, a phaco probe, and/or the like) may be used to cause the nucleus to emulsify, break apart into small pieces, and/or the like while the eye is irrigated and the nuclear material is aspirated. For example, when the control device 340 is set to a third position, the phaco machine 330 may cause the tip of the other handpiece to vibrate, emitting ultrasound waves, ultrasonic energy, and/or the like to emulsify the nucleus and/or break the nucleus into smaller pieces that can be emulsified more easily.

In some implementations, the console 350 may include one or more devices capable of controlling one or more settings and/or parameters of the phaco machine 330 based on the mode in which the phaco machine 330 is operating. For example, the console 350 may include an interface that allows an operator to set an irrigation rate (e.g., when operating the phaco machine 330 in the irrigation mode, the aspiration mode, and/or the phacoemulsification mode), a vacuum pressure and/or aspiration rate (e.g., when operating the phaco machine 330 in the aspiration mode and/or the phacoemulsification mode), a frequency at which to vibrate the tip of the phaco handpiece (e.g., when operating the phaco machine 330 in the phacoemulsification mode), and/or the like. Furthermore, in some implementations, the console 350 may be used to track various metrics related to the cataract surgery (e.g., an elapsed time) and/or the like.

The number and arrangement of devices and networks shown in FIG. 3 are provided as one or more examples. In practice, there may be additional devices, fewer devices, different devices, or differently arranged devices than those shown in FIG. 3. Furthermore, two or more devices shown in FIG. 3 may be implemented within a single device, or a single device shown in FIG. 3 may be implemented as multiple, distributed devices. Additionally, or alternatively, a set of devices (e.g., one or more devices) of environment 300 may perform one or more functions described as being performed by another set of devices of environment 300.

Figure 4:
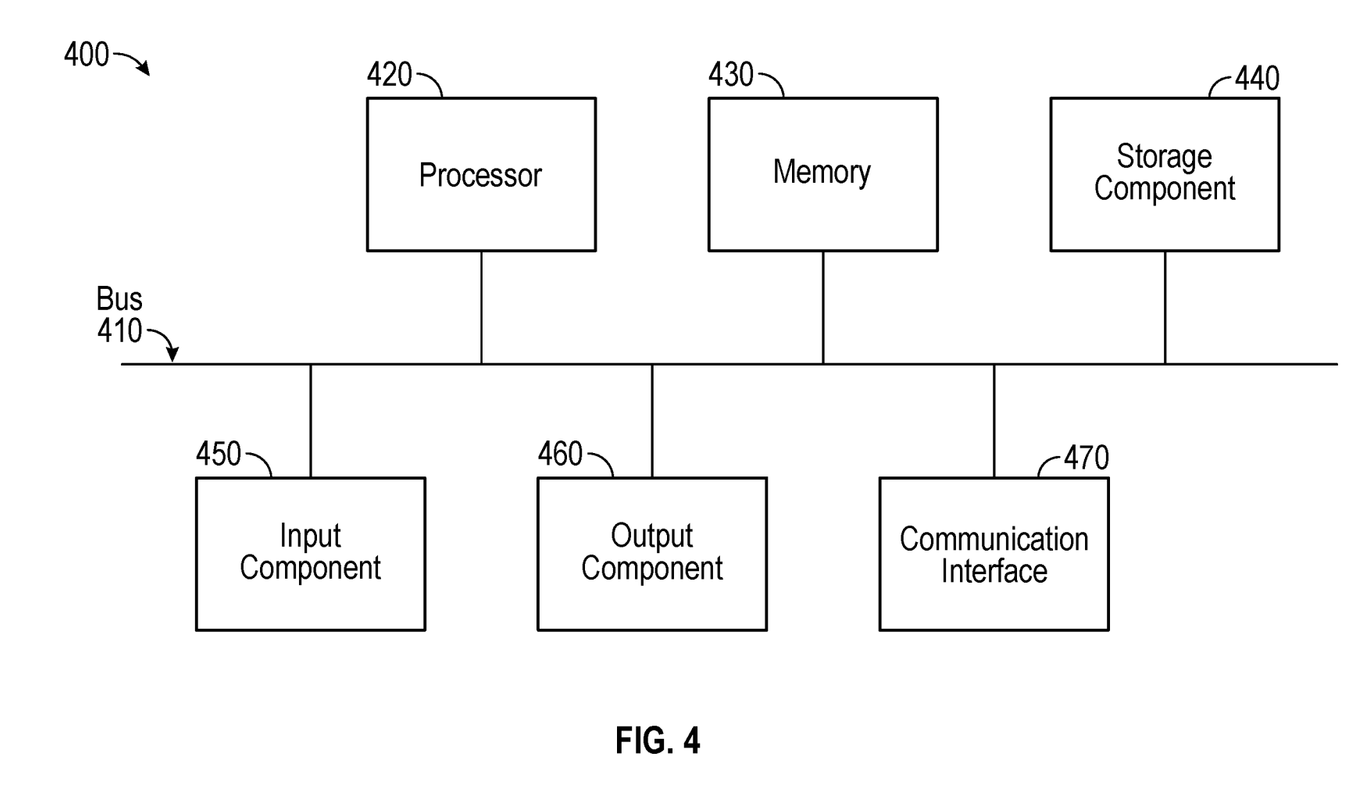
FIG. 4 is a diagram of example components of one or more devices of FIG. 3.

FIG. 4 is a diagram of example components of a device 400. Device 400 may correspond to phaco machine 330, pump 332, control device 340, and/or console 350. In some implementations, phaco machine 330, pump 332, control device 340, and/or console 350 may include one or more devices 400 and/or one or more components of device 400. As shown in FIG. 4, device 400 may include a bus 410, a processor 420, a memory 430, a storage component 440, an input component 450, an output component 460, and a communication interface 470.

Bus 410 includes a component that permits communication among multiple components of device 400. Processor 420 is implemented in hardware, firmware, and/or a combination of hardware and software. Processor 420 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 420 includes one or more processors capable of being programmed to perform a function. Memory 430 includes a random-access memory (RAM), a read only memory (ROM), and/or another type of dynamic or static storage device (e.g., a flash memory, a magnetic memory, and/or an optical memory) that stores information and/or instructions for use by processor 420.

Storage component 440 stores information and/or software related to the operation and use of device 400. For example, storage component 440 may include a hard disk (e.g., a magnetic disk, an optical disk, and/or a magneto-optic disk), a solid-state drive (SSD), a compact disc (CD), a digital versatile disc (DVD), a floppy disk, a cartridge, a magnetic tape, and/or another type of non-transitory computer-readable medium, along with a corresponding drive.

Input component 450 includes a component that permits device 400 to receive information, such as via user input (e.g., a touch screen display, a keyboard, a keypad, a mouse, a button, a switch, and/or a microphone). Additionally, or alternatively, input component 450 may include a component for determining location (e.g., a global positioning system (GPS) component) and/or a sensor (e.g., an accelerometer, a gyroscope, an actuator, another type of positional or environmental sensor, and/or the like). Output component 460 includes a component that provides output information from device 400 (via, e.g., a display, a speaker, a haptic feedback component, an audio or visual indicator, and/or the like).

Communication interface 470 includes a transceiver-like component (e.g., a transceiver, a separate receiver, a separate transmitter, and/or the like) that enables device 400 to communicate with other devices, such as via a wired connection, a wireless connection, or a combination of wired and wireless connections. Communication interface 470 may permit device 400 to receive information from another device and/or provide information to another device. For example, communication interface 470 may include an Ethernet interface, an optical interface, a coaxial interface, an infrared interface, a radio frequency (RF) interface, a universal serial bus (USB) interface, a Wi-Fi interface, a cellular network interface, and/or the like.

Device 400 may perform one or more processes described herein. Device 400 may perform these processes based on processor 420 executing software instructions stored by a non-transitory computer-readable medium, such as memory 430 and/or storage component 440. As used herein, the term "computer-readable medium" refers to a non-transitory memory device. A memory device includes memory space within a single physical storage device or memory space spread across multiple physical storage devices.

Software instructions may be read into memory 430 and/or storage component 440 from another computer-readable medium or from another device via communication interface 470. When executed, software instructions stored in memory 430 and/or storage component 440 may cause processor 420 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 4 are provided as an example. In practice, device 400 may include additional components, fewer components, different components, or differently arranged components than those shown in FIG. 4. Additionally, or alternatively, a set of components (e.g., one or more components) of device 400 may perform one or more functions described as being performed by another set of components of device 400.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

Certain user interfaces have been described herein and/or shown in the figures. A user interface may include a graphical user interface, a non-graphical user interface, a text-based user interface, and/or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, and/or the like). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A device, comprising:
a sleeve having a proximal end and a distal end;
an aspiration lumen disposed concentrically in the sleeve and extending from the proximal end of the sleeve to the distal end of the sleeve,
wherein the aspiration lumen is disposed concentrically in the sleeve to define an irrigation lumen in an annular region between the sleeve and the aspiration lumen; and
a curved aspiration tip, coupled to the sleeve at the distal end of the sleeve, that has multiple aspiration ports configured to draw material into the aspiration lumen from multiple areas when a suction source is used to apply vacuum pressure at a proximal end of the aspiration lumen,
wherein the curved aspiration tip has a radius of curvature based on a human equatorial lens diameter,
wherein the multiple aspirations ports are configured to be arranged consecutively along a curve of the aspiration tip along a width of the curved aspiration tip from one end of the width of the curved aspiration tip to an opposite end of the width of the curved aspiration tip,
wherein the width of the curved aspiration tip is longer than a height of the curved aspiration tip, is longer than a depth of the curved aspiration tip, and wherein the width is along an axis perpendicular to the aspiration lumen, and
wherein the distal end of the sleeve includes one or more irrigation ports arranged to permit irrigation fluid to flow outwardly therefrom.

2. The device of claim 1, wherein the radius of curvature is sharper than the human equatorial lens diameter by an amount that is further based on a diameter at an edge of a capsulorhexis.

3. The device of claim 1, further comprising:
an interface coupling the curved aspiration tip to the distal end of the sleeve,
wherein the interface displaces the curved aspiration tip from a longitudinal axis of the sleeve according to an angular offset.

4. The device of claim 1, wherein the multiple aspiration ports have a diameter in a range from about 0.10 millimeters to about 0.50 millimeters.

5. The device of claim 1, wherein the multiple aspiration ports are arranged according to a spacing that distributes the vacuum pressure over an aggregate surface area of the multiple aspiration ports.

6. The device of claim 1, wherein the curved aspiration tip is integrally coupled to the sleeve.

7. The device of claim 1, wherein the curved aspiration tip is removable from the sleeve.

8. The device of claim 1, wherein the material drawn into the aspiration lumen is cortical material to be removed from a lens of a cataract surgery patient after a nucleus has been removed from the lens of the cataract surgery patient.

9. An aspiration device, comprising:
a curved body having a radius of curvature based on a human equatorial lens diameter;
another body;
an aspiration lumen disposed in the other body and one or more irrigation ports configured to be at a distal end of the other body;
an interface adapted to attach the curved body to a first end of an the aspiration lumen; and
multiple aspiration ports formed in the curved body,
wherein the multiple aspiration ports are configured to draw material into the aspiration lumen from multiple areas when a suction source applies vacuum pressure at a second end of the aspiration lumen while the aspiration lumen is attached to the aspiration device,
wherein the multiple aspiration ports are configured to be arranged consecutively along a curve of the curved body along a width of the curved body from one end of the width of the curved body to an opposite end of the width of the curved body,
wherein the width of the curved body is longer than a height of the curved body, is longer than a depth of the curved body, and along an axis perpendicular to the aspiration lumen, and
wherein the multiple aspiration ports are arranged to distribute the vacuum pressure over an aggregate surface area of the multiple aspiration ports while the suction source applies the vacuum pressure.

10. The aspiration device of claim 9, wherein the radius of curvature is sharper than the human equatorial lens diameter by an amount that satisfies a threshold.

11. The aspiration device of claim 9, wherein the interface is adjustable to permit the curved body to be displaced from a longitudinal axis of the aspiration lumen according to an angular offset in a range from about 10 degrees to about 90 degrees.

12. The aspiration device of claim 9, wherein the multiple aspiration ports include a central port with one or more lateral ports arranged on either side of the central port, a pair of central ports, or a pair of central ports with one or more lateral ports arranged on either side of the pair of central ports.

13. The aspiration device of claim 9, wherein the curved body is made from one or more of a silicone material, a metallic material, or a non-metallic plastic or polymer.

14. The aspiration device of claim 9, wherein the material drawn into the aspiration lumen is one or more of cortical material to be removed from a lens of a cataract surgery patient after a nucleus has been removed from the lens of the cataract surgery patient, or viscoelastic material to be removed from an eye of the cataract surgery patient after an intraocular lens implant has been inserted into the eye of the cataract surgery patient.

15. A system, comprising:
a phacoemulsification machine comprising an irrigation source and a suction source; and
a handpiece, coupled to the phacoemulsification machine, that includes:
a body;
an aspiration lumen disposed concentrically in the body of the handpiece, wherein an annular region between the aspiration lumen and the body of the handpiece defines an irrigation lumen of the handpiece; and
a curved aspiration tip having multiple aspiration ports configured to draw material into the aspiration lumen from multiple areas when the suction source is used to apply vacuum pressure at a proximal end of the aspiration lumen, wherein a distal end of the body includes one or more irrigation ports, wherein the multiple aspiration ports are configured to be arranged consecutively along a curve of the aspiration tip along a width of the curved aspiration tip from one end of the width of the curved aspiration tip to an opposite end of the width of the curved aspiration tip, wherein the width of the curved aspiration tip is longer than a height of the curved aspiration tip, is longer than a depth of the curved aspiration tip, and wherein the width is along an axis perpendicular to the aspiration lumen, and wherein the phacoemulsification machine is adapted to cause irrigation fluid to flow from the irrigation source into the irrigation lumen and out the one or more irrigation ports.

16. The system of claim 15, wherein the multiple aspiration ports are arranged to distribute the vacuum pressure over an aggregate surface area of the multiple aspiration ports.

17. The system of claim 15, wherein the curved aspiration tip has a hammerhead shape with a radius of curvature based on a human equatorial lens diameter.

18. The system of claim 15, wherein an interface between the body and the curved aspiration tip permits adjustment of an angular offset between the curved aspiration tip and a longitudinal axis of the body.

19. The system of claim 15, wherein the material drawn into the aspiration lumen includes one or more of cortical material to be removed from a lens of a cataract surgery patient after a nucleus has been removed from the lens of the cataract surgery patient, or viscoelastic material to be removed from an eye of the cataract surgery patient after the cortical material has been removed and an intraocular lens implant has been inserted into the eye of the cataract surgery patient.

20. The system of claim 15, further comprising:
a control device, coupled to the phacoemulsification machine, to cause the vacuum pressure to be applied at the proximal end of the aspiration lumen and to cause the irrigation fluid to flow from the irrigation source into the irrigation lumen.

* * * * *